United States Patent
Butterfield et al.

(10) Patent No.: US 10,837,436 B2
(45) Date of Patent: Nov. 17, 2020

(54) SYSTEM AND METHOD FOR IMPROVED FLOW UNIFORMITY IN A PERISTALTIC PUMP MECHANISM

(71) Applicant: CAREFUSION 303, INC., San Diego, CA (US)

(72) Inventors: Robert D. Butterfield, Poway, CA (US); Daniel Abal, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 14/885,832

(22) Filed: Oct. 16, 2015

(65) Prior Publication Data
US 2016/0040662 A1 Feb. 11, 2016

Related U.S. Application Data

(62) Division of application No. 13/315,196, filed on Dec. 8, 2011, now Pat. No. 9,163,623.

(51) Int. Cl.
*F04B 43/08* (2006.01)
*F04B 43/12* (2006.01)
(Continued)

(52) U.S. Cl.
CPC ........ *F04B 43/082* (2013.01); *F04B 43/0045* (2013.01); *F04B 43/084* (2013.01);
(Continued)

(58) Field of Classification Search
CPC ...... F04B 43/12; F04B 43/1223; F04B 45/08; F04B 9/042; F04B 43/082; F04B 43/0045;
(Continued)

(56) References Cited

U.S. PATENT DOCUMENTS 3,726,613 A * 4/1973 von Casimir ....... F04B 11/0075
417/477.1
4,728,265 A * 3/1988 Cannon ............. A61M 5/14228
16/225
(Continued)

FOREIGN PATENT DOCUMENTS

| CN | 101529093 A | 9/2009 |
|---|---|---|
| DE | 4035182 C1 | 1/1992 |
| EP | 0214443 A1 | 3/1987 |

OTHER PUBLICATIONS

Australian Examination Report No. 2 for Application No. 2012347768, dated Jul. 7, 2017, 2 pages.
(Continued)

*Primary Examiner* — Bryan M Lettman
(74) *Attorney, Agent, or Firm* — Morgan, Lewis & Bockius LLP

(57) ABSTRACT

A pumping mechanism includes a plurality of peristaltic pumping actuators to compress adjacent portions of a first portion of an at least partially compressible pumping element having an inlet that is upstream of an outlet. The plurality of pumping actuators further reciprocate at a common drive frequency with a first phase offset between each adjacent pair of pumping actuators. The pumping mechanism also includes one compensation actuator to compress a second portion of the compressible pumping element disposed between the first portion and the outlet. The compensation actuator reciprocates at an optimal displacement and at a modulation frequency that is an integer multiple of the fundamental drive frequency and with a second phase offset between the compensation actuator and the adjacent pumping actuator.

22 Claims, 6 Drawing Sheets

(51) Int. Cl.
*F04B 43/09* (2006.01)
*F04B 43/00* (2006.01)
*F04B 9/04* (2006.01)

(52) U.S. Cl.
CPC .......... *F04B 43/09* (2013.01); *F04B 43/1223* (2013.01); *F04B 9/042* (2013.01)

(58) Field of Classification Search
CPC ........ F04B 43/09; F04B 43/08; F04B 43/084; F04B 45/067
See application file for complete search history.

(56) References Cited

U.S. PATENT DOCUMENTS

| | | | |
|---|---|---|---|
| 4,954,046 A | | 9/1990 | Irvin et al. |
| 5,716,194 A | * | 2/1998 | Butterfield ........ A61M 5/16831 417/43 |
| 5,938,413 A | | 8/1999 | Makino et al. |
| 5,980,490 A | * | 11/1999 | Tsoukalis .............. F04B 43/082 417/474 |
| 2006/0173412 A1 | * | 8/2006 | Susi ...................... F04B 43/082 604/123 |
| 2011/0158823 A1 | | 6/2011 | Wang et al. |
| 2011/0264053 A1 | | 10/2011 | Nilsson et al. |
| 2011/0270288 A1 | | 11/2011 | Stergiopulos |

OTHER PUBLICATIONS

Australian Examination Report No. 1 for Application No. 2012347768, dated Jul. 25, 2016, 4 pages.
European Office Action for Application No. 12856266.7, dated Jan. 2, 2017, 4 pages.
European Office Action for Application No. 12856266.7, dated May 27, 2019, 4 pages.
Mexican Office Action and Memo for Application No. MX/a/2014/006627, dated Jun. 7, 2019, 4 pages.
Canadian Office Action for Application No. 2857508, dated Oct. 22, 2018, 8 pages.
Chinese First Office Action for Application No. 201280066166.2, dated Sep. 22, 2015, 6 pages.
Extended European Search Report for Application No. 12856266.7, dated Nov. 3, 2015, 7 pages.
International Search Report and Written Opinion for Application No. PCT/US2012/068271, dated Mar. 25, 2013, 9 pages.
Chinese Second Office Action for Application No. 201280066166.2, dated May 18, 2016, 5 pages excluding translation.

* cited by examiner

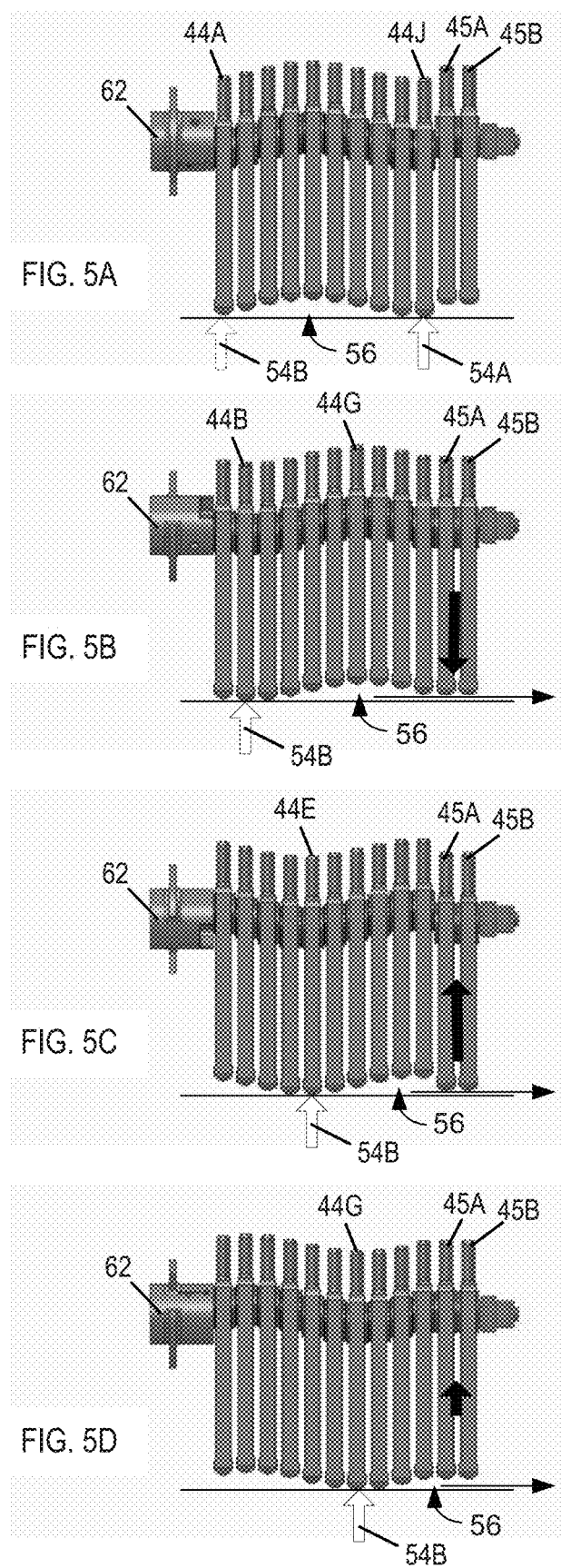

SYSTEM AND METHOD FOR IMPROVED FLOW UNIFORMITY IN A PERISTALTIC PUMP MECHANISM

CROSS-REFERENCES TO RELATED APPLICATIONS

This application is a divisional of U.S. patent application Ser. No. 13/315,196, entitled SYSTEM AND METHOD FOR IMPROVED FLOW UNIFORMITY IN A PERISTALTIC PUMP MECHANISM, filed on Dec. 8, 2011, which is hereby incorporated by reference in its entirety for all purposes.

BACKGROUND

Field

The present disclosure is related to peristaltic pumping systems and, in particular, intravenous (IV) pumps that include peristaltic pumping systems.

Description of the Related Art

Patients in hospitals often receive medications and medical fluids via infusion using an IV pump. One traditional configuration of IV pump uses peristaltic manipulation of a segment of tubing of an IV set to create the flow of medical fluid to the patient. This type of pumping mechanism is simple and reliable and the pumping segment of the IV set is a straight piece of flexible tubing, making this a relatively low-cost IV set.

One drawback to a peristaltic pumping system is that the flow rate varies with time as the "wave" created by the motion of the peristaltic actuators reaches the outlet of the pumping system. The instantaneous flow rate varies about an average flow rate. This variation can result in clinically significant instability of the patient when medications having short response times (half-lives) are being administered to regulate the function of critical organ systems.

SUMMARY

It is desirable to provide a system and method of peristaltic pumping that has a reduced amount of variation in the net output flow rate.

In certain embodiments, a pumping mechanism is disclosed that includes a plurality of peristaltic pumping actuators configured to sequentially compress adjacent sections of a first portion of an at least partially compressible pumping element having an inlet and an outlet that is downstream of the inlet. The plurality of pumping actuators are further configured to reciprocate with a motion comprising a fundamental drive frequency. A last pumping actuator of the plurality of pumping actuators is nearest to the outlet. The pumping mechanism also includes at least one compensation actuator arranged to selectively compress a second portion of the at least partially compressible pumping element that is disposed between the first portion and the outlet of the at least partially compressible pumping element. The at least one compensation actuator is configured to reciprocate with a motion comprising the fundamental drive frequency at a phase shift relative to the last pumping actuator.

In certain embodiments, a pumping system for use with an intravenous (IV) set having an outlet is disclosed. The pumping system includes a drive motor configured to rotate, a drive shaft coupled to the drive motor, and a plurality of pumping cams disposed in a row along the drive shaft and coupled to the drive shaft. The plurality of pumping cams have common profiles with common rotational offsets between each pair of adjacent pumping cams. The plurality of pumping cams includes a last pumping cam. The pumping system also includes a compensation cam fixedly coupled to the drive shaft adjacent to the last pumping cam. The compensation cam is rotationally offset relative to the last pumping cam. The pumping system also includes a plurality of pumping actuators respectively coupled to the plurality of pumping cams. The pumping actuators are configured to peristaltically manipulate adjacent sections of a first portion of the IV set when the drive shaft is rotated. The pumping system also includes a compensation actuator coupled to the compensation cam. The compensation actuator is arranged to selectively compress a section of a second portion of the IV set that is disposed between the first portion and the outlet.

In certain embodiments, a method is disclosed that includes the steps of peristaltically manipulating a first portion of an at least partially compressible pumping element having an inlet that is upstream of an outlet, the first portion disposed between the inlet and the outlet, to cause a fluid to flow out of the outlet at a first rate that varies periodically between a first maximum and a first minimum and manipulating a second portion of the at least partially compressible pumping element that is disposed between the first portion and the outlet to cause the fluid to flow out of the outlet at a second rate that varies periodically about zero, wherein the sum of the first and second flow rates has a second maximum and a second minimum that are less than the respective first maximum and first minimum.

In certain embodiments, a pumping mechanism is disclosed that includes a peristaltic pumping mechanism having an inlet and an outlet. The pumping mechanism is configured to receive a fluid through the inlet and provide an output flow of the fluid through the outlet at a rate that varies periodically over time about a nominal flow rate. The pumping mechanism also includes a variable volume having an inlet fluidically coupled to the outlet of the pumping mechanism and an outlet. The volume is configured to vary synchronously with the periodic variation of the output flow.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 5A-5D depict sequential configurations of the pumping system of FIG. 3 during operation according to certain aspects of this disclosure.

DETAILED DESCRIPTION

The following description discloses embodiments of a system and method for providing improved uniformity of flow from a peristaltic pumping system. In certain embodiments, the pumping system includes at least one compensation actuator that may be driven by a compensation cam coupled to the same drive shaft that drives the pumping cams and thereby actuates the pumping actuators or may be motivated by a separate motive source such as a linear stepper motor. In certain embodiments, the speed of rotation of the drive shaft is modulated to further smooth the flow rate of the fluid delivered by the pumping system.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology Like components are labeled with identical element numbers for ease of understanding.

Figure 1A:
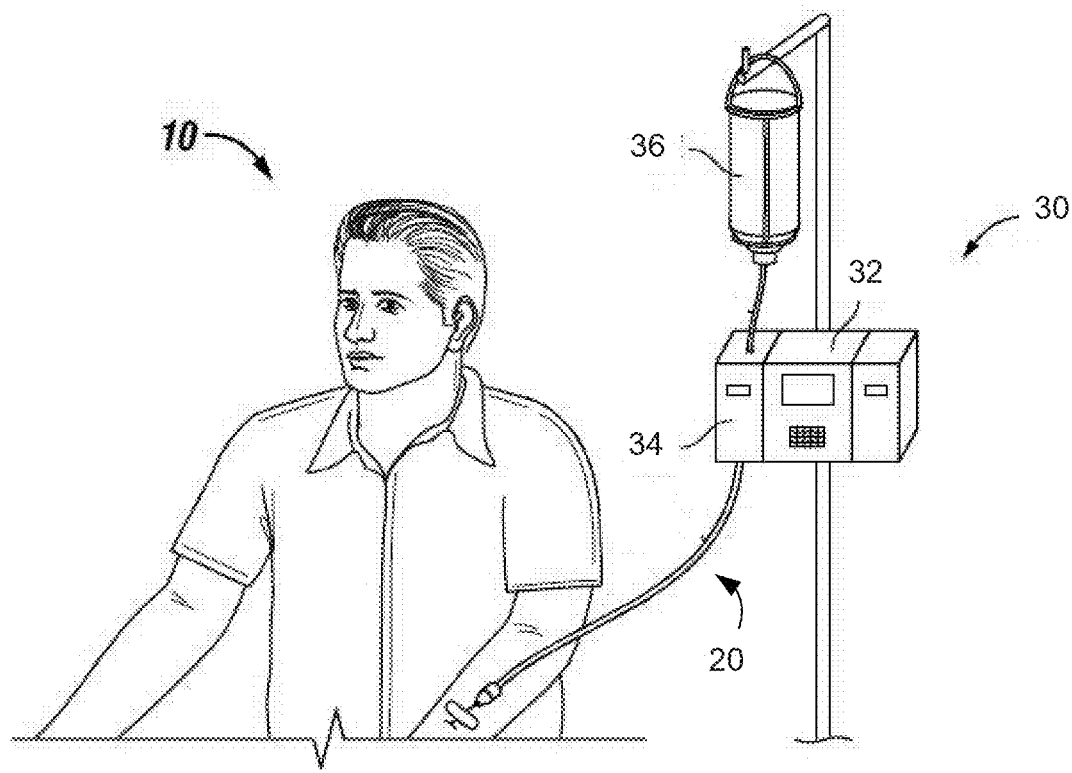
FIG. 1A depicts a patient receiving an infusion of a medical fluid using an IV pump.

FIG. 1A depicts a patient 10 receiving an infusion of a medical fluid using an IV pump 30. In this example, the IV pump 30 includes a control unit 32 and a pumping module 34. A fluid container 36 is hung at or above the patient's head and connected via an IV set 20 to the IV pump module 34 and then to the patient 10.

Figure 1B:
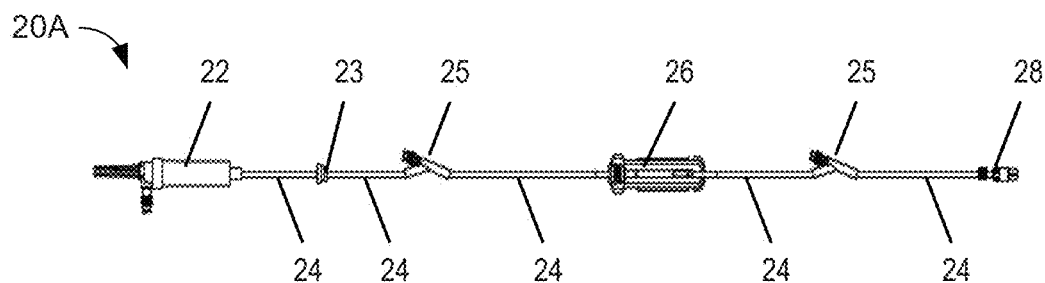
FIG. 1B depicts an example IV set.

FIG. 1B depicts an example IV set 20A. This example IV set 20 includes a drip chamber with bag spike 22 that is configured to connect to a fluid source such as fluid container 36 of FIG. 1A. The drip chamber 22 is connected through tubing 24 to a pumping segment 26 which is then connected through additional tubing 24 to a fitting 28. In this example, fitting 28 is a needleless Luer connector suitable for connection to any vascular access device (VAD) (not shown) such as an intravenous needle. Pumping segment 26 is configured to mate with a pumping module 34 and be manipulated by the pumping mechanism (not visible) within the pumping module 34 to cause fluid to flow from the bag spike 22 to the fitting 28. The example IV set 20A of FIG. 1B also includes a check valve 23 and two needleless access ports 25.

Figure 1C:
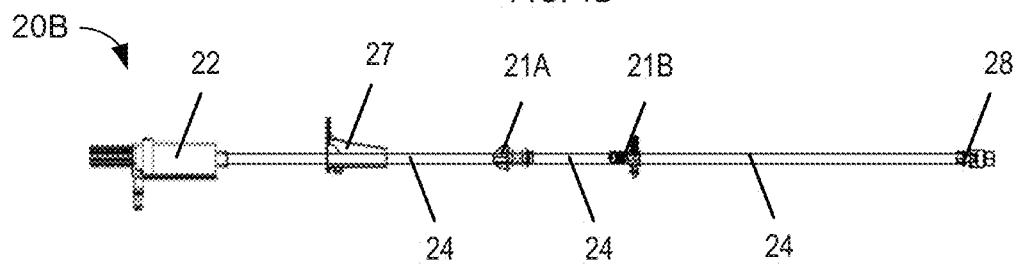
FIG. 1C depicts a second example IV set.

FIG. 1C depicts a second example IV set. This example IV set 20B includes a drip chamber 22 that is functionally the same as the bag spike of FIG. 1B. The drip chamber 22 is connected through tubing 24 to the fitting 28. In the IV set 20B, the pumping segment is a length of the same tubing 24 with locating fittings 21A and 21B coupled to the tubing 24. This style of IV set may be less expensive that the IV set 20A. The example IV set 20B of FIG. 1C also includes a roller clamp 27.

Figure 2A:
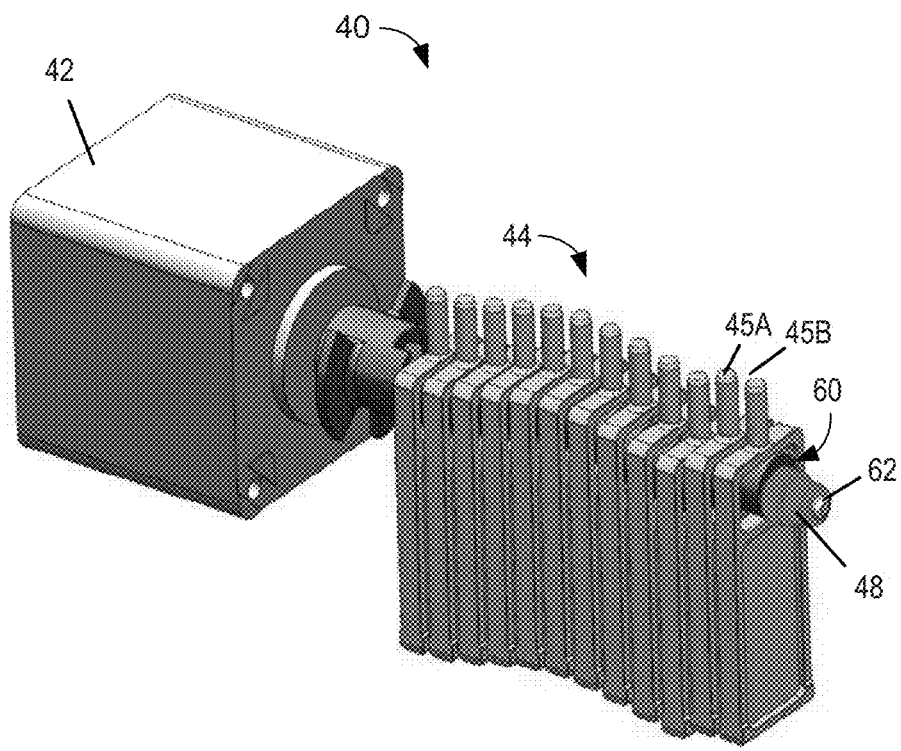
FIG. 2A is a perspective view of an exemplary embodiment of a pumping system included in the pumping module of FIG. 1A according to certain aspects of this disclosure.

FIG. 2A is a perspective view of an exemplary embodiment of a pumping system 40 included in the pumping module 34 of FIG. 1A according to certain aspects of this disclosure.

The pumping system 40 includes a motor 42 that is coupled to a drive shaft 62 with a bearing element 48 positioned at the end of the drive shaft 62. The bearing element 48 is configured to mate with the casing (not visible in FIG. 2A) to support the end of drive shaft 62. A series of cams 60 are arranged along the drive shaft 62 and a matching series of actuators 44 and 45A, 45B are arranged over the respective pumping cams 60. The arrangement of cams 60 is discussed in greater detail with respect to FIG. 3.

Figure 2B:
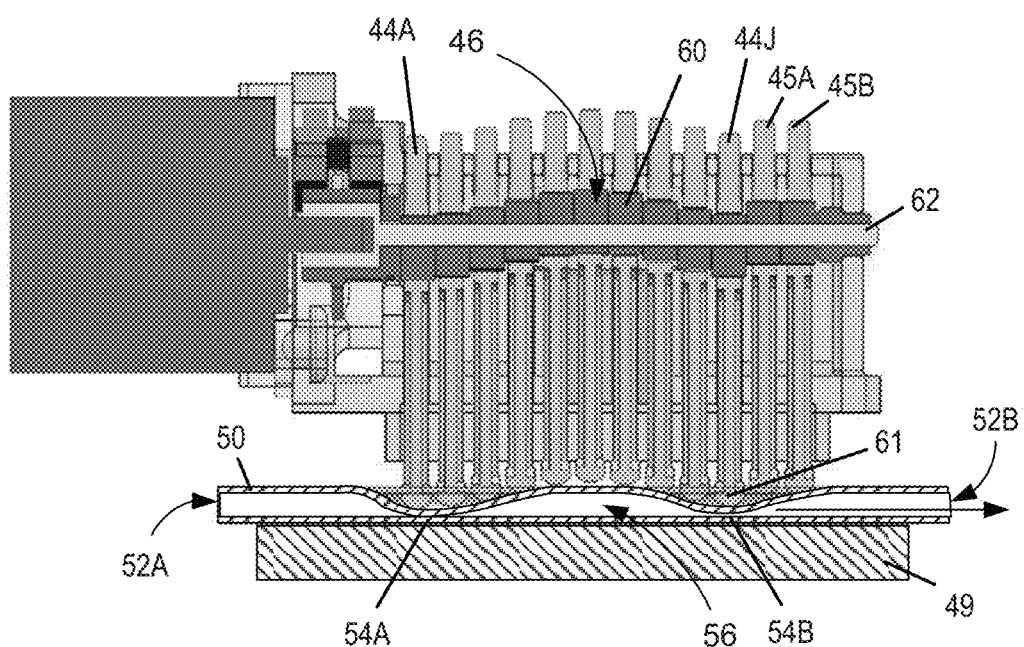
FIG. 2B is a lateral cross-section view of the pumping system of FIG. 2A according to certain aspects of this disclosure.

FIG. 2B is a lateral cross-section view of the pumping system 40 of FIG. 2A according to certain aspects of this disclosure. The plurality of cams 60 of camshaft 46 are arranged in a row along the drive shaft 62 and are fixedly attached to the drive shaft 62. Each pumping cam 60A-60J is attached at a incremental rotational (phase) location about the shaft—typically 36° in the example of FIG. 2B. As the shaft 62 rotates, the actuator moves in a sinusoidal reciprocating motion. In this example, the cams 60 are circular and are attached to the drive shaft 62 at an offset location from center such that the surface of the cams 60 vary in distance from the drive shaft 62. Cams 60 of this type are known to those of skill in the art. Each of the actuators 44A-44J has an opening that fits over one of the cams 60. As the drive shaft 62 rotates, each of the actuators 44 reciprocates up and down at a frequency that matches the rotational rate of the drive shaft 62. The embodiment of FIG. 2B includes two compensation actuators 45A, 45B driven by cams 64A and 64B that are described in greater detail with respect to FIGS. 5A-5D. The pumping system 40 includes a platen 49 located underneath the tips 61 of the actuators 60, and the pumping system 40 is configured to accept a flexible tube 50 between the actuators 44 and the platen 49. In this example, the flexible tube 50 is part of the pumping segment 26 of the IV set 20 of FIG. 1B. As each actuator 44 descends toward the platen 49, the tip 61 compresses the tube 50 and, when an actuator 44 is fully descended, compressed the tube 50 sufficiently to form a pinch point or an occlusion 54A, 54B that blocks flow through the tube 50. In a peristaltic pump such as the pumping system 40 shown in FIGS. 2A and 2B, it can be seen that the cams 60 are arranged such that the vertical positions of the actuators 44 form a "wave" pattern. As the drive shaft 62 turns, the "wave" moves from left to right, in this example, thereby forcing a control chamber 56 of fluid within the tube 50 to travel to the right and eventually be expelled from outlet 52B as indicated by the arrow. At the same time, fluid is drawn in through the inlet 52A into a new control chamber 56 formed as the leftmost actuators 44 descend. In certain embodiments, the driveshaft 62 is operated at a constant angular velocity, thereby producing a flow that is irregular, i.e. the flow stopping completely when the occlusion is under actuator 44J and reaching higher-than-average flow rates when the occlusion is under actuators 44B-44E.

In certain embodiments, the actuators 44 are configured to manipulate a non-tubular pumping element (not shown) in place of the tube 50. In certain embodiments, the pumping element comprises a rigid U-channel with a flexible membrane covering the open side of the U-channel so as to form an at least partially compressible pumping element. The operation and behavior if this at least partially compressible pumping element is the same as described with respect to the tube 50 in this disclosure.

Figure 3:
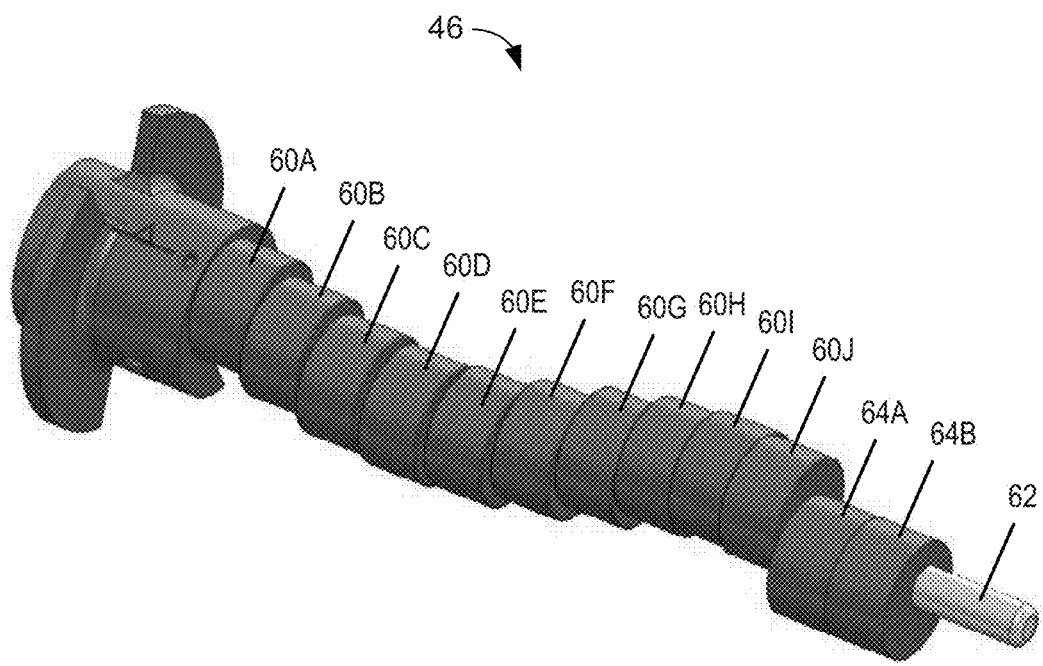
FIG. 3 is a perspective view of an exemplary camshaft according to certain aspects of this disclosure.

FIG. 3 is a perspective view of an exemplary camshaft 46 according to certain aspects of this disclosure. Pumping cams 60A-60J are arranged along the drive shaft 62 with, in this example, two compensation cams 64A and 64B disposed at the downstream end of the drive shaft 62. The function of the compensation cams 64A, 64B is described in greater detail with respect to FIGS. 5A-5D. In this example, the pumping cams 60A-60J have identical profiles that will cause the respective actuators 44 to reciprocate up and down with a generally sinusoidal motion at the frequency of the rotation of the drive shaft 62. For example, if the drive shaft 62 is rotating at a constant speed of 1 revolution per second (rev/sec), the motion of the actuators 44 will be an approximate sinusoid with a frequency of 1 Hz. If the rotational speed of the drive shaft 62 is varied, for example the speed varies sinusoidally about a steady-state speed of 1 rev/sec, then the motion of the actuators 44 will be more complex motion with a fundamental frequency of 1 Hz and secondary frequencies related to the rate of variation of the drive shaft speed. In certain embodiments, the speed of the drive shaft 62 varies at a rate that is a integer multiple of the fundamental speed. In certain embodiments, the speed of the drive shaft 62 varies at a rate that is twice that of the fundamental rotational speed.

In certain embodiments, the compensation is provided by the shape of the compensation cams 64A, 64B that are moving at the same angular velocity as the pumping cams 60A-60J. The effectiveness of compensation depends on choice of cam geometry, phase with respect to pump cams and width. In certain embodiments, the profile of at least one of the compensation cams 64A, 64B is a non-circular shape. In certain embodiments, the shape is sinusoidal with a phase and amplitude that comprise a 1st harmonic modulation of a circular profile. In certain embodiments, the shape of at least one of the compensation cams 64A, 64B comprises a phase and amplitude that comprise a 2nd harmonic modulation of the shape of the cam.

In certain embodiments, the compensation is provided by modulation of the angular velocity of the one or more of the compensation cams 64A, 64B during each rotation either by use of gear linkages, for example if driven from a common motor with the pumping cams 60A-60J, or by direct control of a separate drive motor coupled to the compensation cams 64A, 64B. In certain embodiments, the modulation frequency is twice the fundamental drive frequency. In certain embodiments, the instantaneous angular velocity varies to produce a variable flow that comprises a first harmonic of the flow induced by the pumping cams 60A-60J. In certain embodiments, the instantaneous angular velocity varies to produce a variable flow that comprises a second harmonic of the flow rate variation. In certain embodiments, the instantaneous angular velocity varies to produce a variable flow that comprises higher harmonics of the flow rate variation.

Figure 4A:
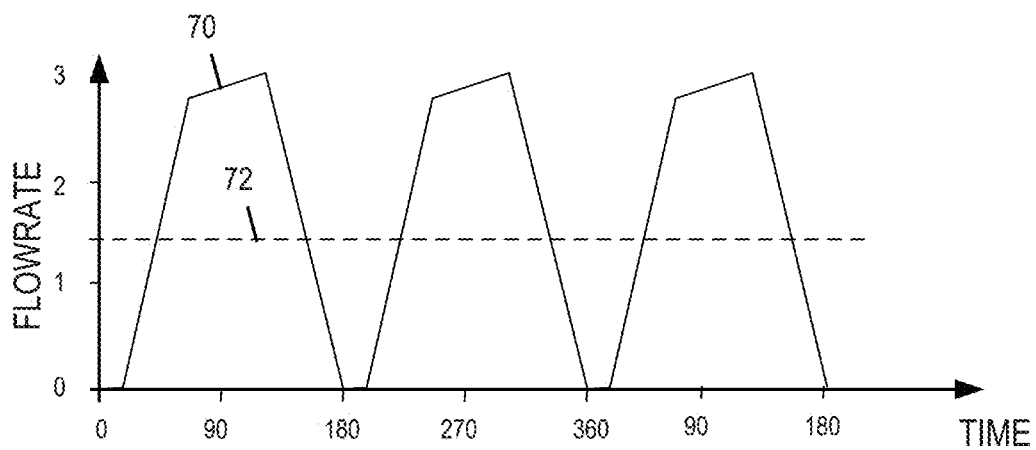
FIG. 4A depicts the output flow of a peristaltic pumping system having twelve pumping actuators without any compensation actuators and its driveshaft rotating at a constant angular velocity according to certain aspects of this disclosure.

FIG. 4A depicts the output flow of a peristaltic pumping system 40 having twelve pumping actuators 44 without any compensation actuators 46 and its driveshaft 62 rotating at a constant angular velocity according to certain aspects of this disclosure. The twelve pumping actuators 44A-44J and 45A and 45B are driven by pumping cams 60A-60J and 64A and 64B having uniform incremental phase offsets in rotational orientation with respect to the pumping cams 60 on each side. For the example of FIG. 4A, pumping cam 60E is positioned 30° ahead of pumping cam 60D and 30° behind pumping cam 60F. As the drive shaft 62 rotates at a constant speed, the occlusive wave pattern described with respect to FIG. 2B will travel the length of the row of twelve pumping cams 60A-60J and 64A and 64B and produce a flow having an average flow rate shown as reference line 72 and an actual flow rate over time that is shown by line 70. The flow rate 70 varies at the same frequency as the rotation of the drive shaft 62.

Figure 4B:
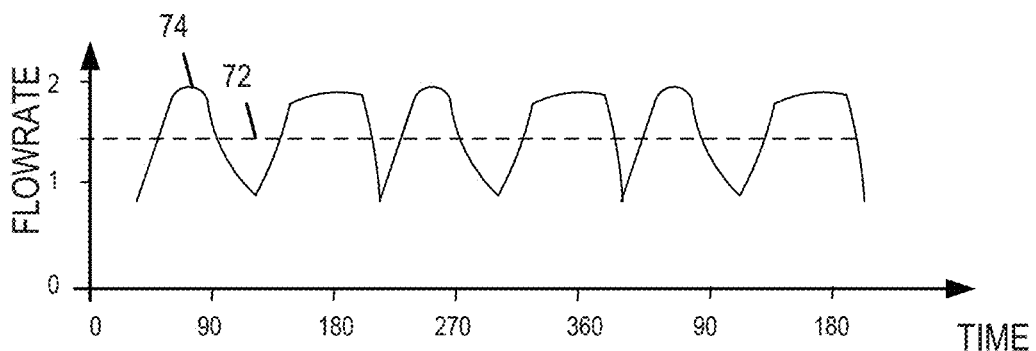
FIG. 4B depicts the output flow of a pumping system having ten pumping actuators and two compensation actuators as shown in FIG. 3 and its driveshaft rotating at a constant angular velocity according to certain aspects of this disclosure.

FIG. 4B depicts the results of the same simulation used for FIG. 4A configured to calculate the output flow of a pumping system 40 having ten pumping actuators 44A-44H and two compensation actuators 45A, 45B as shown in FIG. 3 and its driveshaft 62 rotating at a constant angular velocity according to certain aspects of this disclosure. In this example, the compensation cams 64A, 64B have a similar profile to the pumping cams 60A-60J but with a reduced "lift," i.e. the range of reciprocating motion of the compensation actuators 45A, 45B is less than that of the pumping actuators 44A-44J. This reduced lift results in incomplete compression, or occlusion, of the tubing 50. The two compensation cams 64A, 64B are rotationally aligned with each other and offset from the adjacent pumping actuator 44H by approximately 180°. The resulting instantaneous flow rate 74 and the average flow rate 72 are plotted to the same time and flow rate scales as FIG. 4A. The motor 42 of pumping system 40 of FIG. 4B was run at a slightly higher average angular rate than the pumping system 40 of FIG. 4A in order to provide the same average flow rate, as the volume of the control chamber 56 is slightly smaller with a ten-pumping-actuator configuration than with a twelve-pumping-actuator configuration. It can be seen that the maximum variation in flow rate is lower in the pumping system 40 of FIG. 4B, i.e. a pumping system 40 with compensation cams 64A, 64B and compensation actuators 45A, 45B. In certain embodiments, the variation is reduced further using modulation of the rate of rotation of one or both of the pumping cams 60A-60J and the compensation cams 64A, 64B.

In the same way that the output flow may vary by 100% as shown in FIG. 4A, the inlet flow, i.e. the flow rate of fluid being drawn into the peristaltic pumping mechanism 46 through the inlet 52A, varies with time. In certain configurations of infusion systems, such as when a primary source and a secondary source of fluid are joined at a "Y" junction wherein the primary source includes a flow control valve intended to prevent flow until the secondary source of fluid is depleted, the negative pressure spike may cause unintended flow from the primary source. In other configurations, a negative pressure spike in the lines from the fluid source to the pump, induced by a sudden surge in the intake rate from the pump, may create bubbles in the fluid. In these configurations, it is desirable to have a steady inflow rate of fluid drawn into the IV pump. In certain embodiments, one or more intake compensation cams (not shown in FIG. 3) are provided adjacent to pumping cam 60A and intake compensation actuators (not shown in FIG. 2A or 2B) are provided adjacent to actuator 44A to selectively compress a portion of tube 50 between the inlet 52A and the point of contact of the actuator 44A with the tube 50 so as to smooth the inflow rate of fluid through the inlet. The intake compensation cams function in much the same was as the compensation cam 64A, 64B in that the intake compensation cams cause the respective intake compensation actuators to move out of phase with the first pumping actuator 44A. By expanding a variable volume under the intake compensation actuators while the first pumping cam 44A is descending or fully compressing the tube 50 and collapsing the variable volume while the first pumping actuator 44A is ascending, the intake flow rate is smoothed similarly to smoothing of the output flow rate by the compensation actuators 45A, 45B.

FIGS. 5A-5D depict sequential configurations of the pumping system 40 of FIG. 3 during operation according to certain aspects of this disclosure. FIG. 5A depicts the pumping system 40 at the point in rotation of drive shaft 62 where a pinch point indicated by the arrow 54A is under the pumping actuator 44J and the compensation actuators 45A, 45B are at the maximum height above the platen (not shown in FIGS. 5A-5D). Pumping actuator 44A is almost at its maximum extension and about to form another pinch point at the location shown by the dashed-line arrow 54B to form a control chamber 56.

FIG. 5B depicts the same pumping system 40 of FIG. 5A after the drive shaft 62 has rotated approximately 90°. The pinch point 54B has been formed and has moved toward the right from under pumping actuator 44A to a position under pumping actuator 44B, thereby moving the control chamber 56 to the right. The pumping actuator 44J has moved upward, thereby opening the former pinch point 54A and allowing a portion of the fluid in control chamber 56 to flow to the right. The compensation actuators 45A, 45B have moved downward, thereby displacing some of the fluid in the tube that is under the compensation actuators 45A, 45B. This displaced fluid will also flow to the right, augmenting the flow induced by the movement of pinch point 54B.

The benefit of the compensation actuators 45A, 45B is related to the shape of the control chamber 56. The flow of liquid from the control chamber 56 past the compensation actuators 45A, 45B is a function of the volume of the control chamber under pumping actuator 44J at any instant. In the position of FIG. 5B, the volume of the control chamber 56 under pumping actuator 44J is relatively small, compared to the maximum volume of the control chamber 56 under pumping actuator 44G at this same moment in time. The flow rate is therefore also relative low and would be equivalent to one of the low points in the flow rate of FIG. 4A.

However, the downward motion of the compensation actuators 45A, 45B at this same time creates additional flow such that the total flow leaving the pumping system 40 is higher than it would be without the compensation actuators 45A, 45B. It will be seen, with respect to FIG. 5D, that the opposite effect occurs at the time of maximum flow from the control chamber 56, thereby producing a flow rate similar to that of FIG. 4B.

FIG. 5C depicts the pumping system 40 after the drive shaft 62 has approximately rotated an additional 90° from the configuration of FIG. 5B. At this point in time, the pinch point 54B has moved rightward, i.e. toward the patient, and is now located under pumping actuator 44E and the highest point of control chamber 56 is under pumping actuator 44J. The flow rate from the control chamber 56 is at its maximum rate at this time. The compensation actuators 45A, 45B have passed their maximum extension and reversed their direction of motion and are now expanding the volume of the portion of the tube 50 that is under the compensation actuators 45A, 45B. This expansion of tube 50 absorbs some of the fluid being expelled from control chamber 56, thereby reducing the total flow rate of fluid leaving the pumping system 40. Thus, the upward motion of the compensation actuators 45A, 45B reduces the maximum instantaneous flow rate of fluid leaving the pumping system 40 and the downward motion of the compensation actuators 45A, 45B increases the minimum flow rate of liquid leaving the pumping system 40, thereby producing the more-uniform flow rate shown in FIG. 4B compared to the non-compensated flow rate shown in FIG. 4A.

FIG. 5D depicts the pumping system 40 after the drive shaft 62 has approximately rotated an additional 90° from the configuration of FIG. 5C. The compensation actuators 45A, 45B are still moving upward but are slowing as they approach their maximum upward position. The amount of fluid being diverted from the flow rate from the control chamber 56 is reduced compared to the configuration of FIG. 5C, and the flow rate from the control chamber 56 is also reduced as the trailing edge of the control chamber 56 approaches the position under pumping actuator 44J. After another 90° of rotation, the pumping system 40 will have returned to the position of FIG. 5A, thereby completing one cycle of motion. In certain embodiments, the compensation actuators 45A, 45B are configured to create a sinusoidal flow with a maximum additive flow, i.e. flow to the right and out of the pumping system 40, when the adjacent pumping actuator 44J is maximally displaced toward the tube 50 (not shown in FIGS. 5A-5D) and a maximum subtractive flow, which can be thought of as a negative flow that effectively absorbs a portion of the fluid being expelled from the control chamber 56, when the adjacent pumping actuator 44J is maximally displaced away from the tube 50.

In the embodiment shown in FIGS. 5A-5D, the rotational position of the pair of compensation cams 64A, 64B, and therefore the motion of compensation actuators 45A, 45B, are identical. In certain embodiments, the rotational positions of compensation cams 64A, 64B are offset from each other. In certain embodiments, the maximum lift of compensation cam 64B is different from the lift of compensation cam 64A.

Additionally, in certain embodiments, the speed of rotation of the drive shaft 62 is constant while in certain embodiments, the speed of rotation of the drive shaft 62 varies about an average speed. In certain embodiments, the variation in speed of rotation of the drive shaft 62 is modulated at a frequency that is twice the fundamental frequency of rotation. In certain embodiments, the phase relation of the modulation angular velocity with respect to the pumping and compensating cams is adjusted so as to further reduce variation in the flow rate. In certain embodiments, the variation in rotational speed of the drive shaft 62 is accomplished with a mechanical system between the drive motor 42 and the drive shaft 62. In certain embodiments, the variation in rotational speed of the drive shaft 62 is accomplished by modulating the speed of the drive motor 42.

Figure 6:
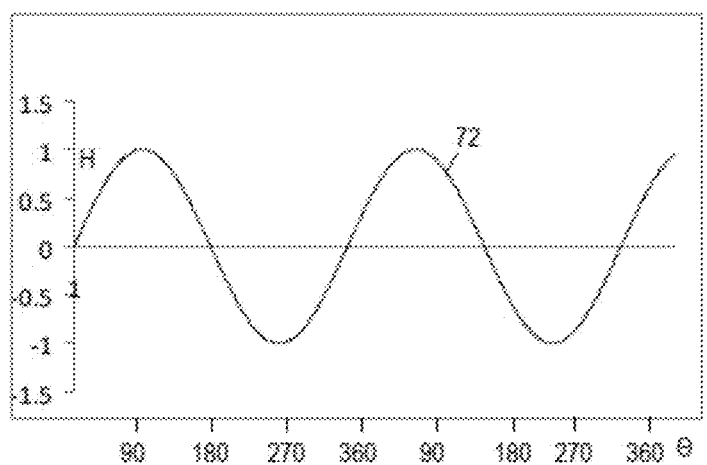
FIG. 6 depicts the fundamental displacement curve of an actuator driven by a circular offset cam according to certain aspects of this disclosure.

FIG. 6 depicts the fundamental displacement curve 72 of an actuator 44 driven by a circular offset cam 60 according to certain aspects of this disclosure. As a circular cam 60 is offset from the axis of rotation, i.e. the shaft 62 shown in FIG. 3, the displacement profile 72 of the associated actuator 44 will reciprocate with a motion comprising a fundamental modulation frequency and an approximately sinusoidal shape. In certain embodiments, a first compensation actuator 45A is located adjacent to a last pumping actuator 44J of the plurality of pumping actuators 44A-44J, as shown in FIG. 2B. The compensation actuator 45A reciprocates with a motion having a fundamental frequency that is phase shifted relative to the fundamental drive frequency of the last pumping actuator 44J. In certain embodiments, the phase shift between compensation actuator 45A and pumping actuator 44J is 180°, i.e. the compensation actuator 45A reaches its maximum height as the pumping actuator 44J reaches its minimum height. In certain embodiments, the phase shift between compensation actuator 45A and pumping actuator 44J is between 90° and 270°.

Figure 7:
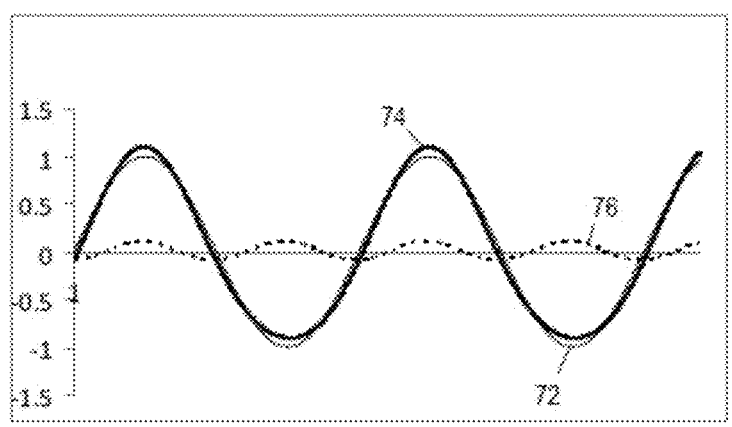
FIG. 7 depicts the displacement curve of an actuator driven by a cam having a shape that incorporates a second harmonic according to certain aspects of this disclosure.

FIG. 7 depicts the displacement curve 74 of an actuator 44 driven by a cam 60 having a shape that incorporates a second harmonic according to certain aspects of this disclosure. The shape of the second harmonic alone is shown by curve 76. It can be seen that curve 76 has a frequency that is twice that of curve 72. Curve 74 is the summation of curves 72 and 76 and it can be seen that the positive displacement peak of curve 74 is greater than that of curve 72 while the negative displacement peak of curve 74 is less than, i.e. more positive, than the curve 72.

Figure 8:
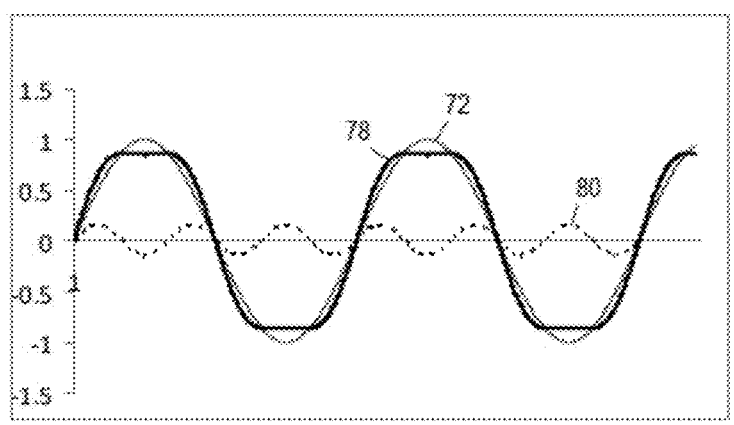
FIG. 8 depicts the displacement curve of an actuator driven by a cam having a shape that incorporates a third harmonic according to certain aspects of this disclosure.

FIG. 8 depicts the displacement curve 78 of an actuator 44 driven by a cam 60 having a shape that incorporates a third harmonic according to certain aspects of this disclosure. Curve 80 illustrates the shape of the third harmonic and it can be seen that the frequency is three times that of curve 72. Curve 78 is the summation of curves 72 and 80 and can be seen to be flat-topped and less than curve 72 for both the positive and negative peaks.

Figure 9:
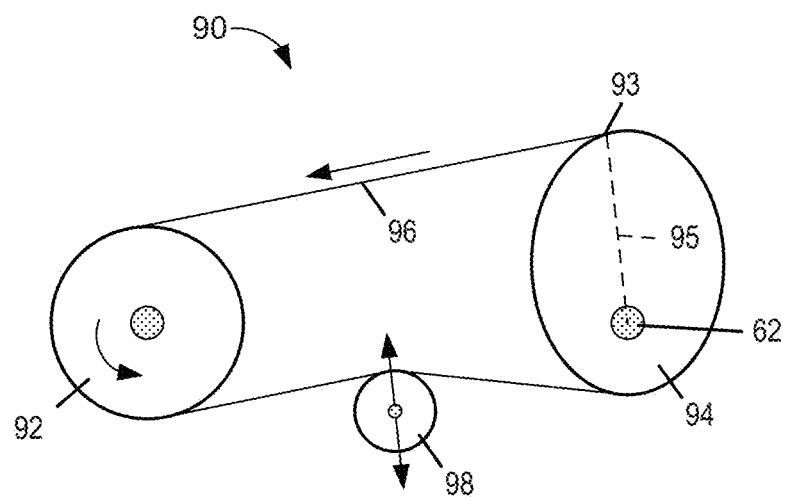
FIG. 9 depicts an exemplary embodiment of a variable speed transmission according to certain aspects of this disclosure.

FIG. 9 depicts an exemplary embodiment of a variable speed transmission 90 according to certain aspects of this disclosure. In this embodiment, a drive wheel 92 having a circular profile is driven by the motor 42 (not shown in FIG. 9) at a constant angular speed. The circular drive wheel is coupled through a drive belt 96 to a cam wheel 94 that is coupled to the driveshaft 62. The cam wheel 92 has, in this example, an elliptical profile (not shown to scale). As the drive wheel 92 turns at a constant speed, the cam wheel 96 will turn at a variable speed where the instantaneous angular speed is a function of the instantaneous offset distance 95 from the center of rotation of the cam wheel 94 to the point of contact 93 between the drive belt 96 with the cam wheel 94. A take-up wheel 98 is biased to apply a lateral force to the drive belt 96 so as to take up any slack as the cam wheel 94 rotates.

It will be apparent to those of skill in the art that, based on the principles disclosed in FIGS. 6-8, a displacement curve of arbitrary shape can be formed by use of a cam that comprises one or more harmonics of the fundamental harmonic of FIG. 6 similar to the formation of an arbitrary periodic wave form using a Fourier series. Each harmonic component may have an independent magnitude and phase angle with respect to the magnitude and phase of the fundamental curve.

Another approach to cam shaping is to first determine the desired displacement profile and then empirically determine the cam shape that produces this profile. As the contact point between the actuator and the cam may shift sideways, i.e. perpendicular to a line parallel to the direction of motion of the actuator, as the cam rotates, the design process to determine a cam shape that produces the desired displacement curve may be an iterative process. A peristaltic pump having a compensation cam with a fundamental offset circular profile modified by second and fourth harmonic profiles will therefore have six independent variables that can be varied to reduce the variation in the output flow. In certain embodiments, one or more of the compensation cams 64A, 64B are shaped as described herein to reduce the variation in the net output flow of a peristaltic pump below the variation accomplished using purely circular cam profiles for compensation cams 64A, 64B.

In certain embodiments, the variation in output flow can be further reduced by varying the rate of rotation of the shaped compensation cam. Using the reference numbering of components in FIG. 3, if the pumping cams 60A-60J are mounted to a first shaft rotating a constant angular velocity and the compensation cams 64A, 64B can rotate at a variable speed, such as by coupling to the drive motor through a variable transmission or coupling to a separate variable-speed motor, then the flow variations of the compensation cams 64A, 64B can be further adjusted by cyclically varying the rotational speed of the compensation cams.

The disclosed pumping systems and methods provide a flow of fluid that is more uniform than the flow of a conventional peristaltic pump. The addition of compensation actuators downstream of the peristaltic pumping actuators and the offset in motion of the compensation actuators with respect to the peristaltic motion of the pumping actuators reduces the maximum flow rate and increases the minimum flow rate, thereby producing a more uniform flow rate over time compared to the variation in flow rate of a traditional peristaltic pump. The compensation cams may be shaped with higher-order harmonics added to the fundamental circular profile of the compensation cams to reduce the residual variation present using purely circular compensation cams. In addition, the speed of the drive shaft may also be varied to further reduce the variation in the net output flow rate. Use of a transmission or linkage to vary the speed of the drive shaft while the motor rotates at a constant speed may avoid noise, vibration, and cost associated with providing a variable-speed motor.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Unless specifically stated otherwise, the term "some" refers to one or more.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A method, comprising:
peristaltically manipulating a first portion of an at least partially compressible pumping element having an inlet that is upstream of an outlet, the first portion disposed between the inlet and the outlet, to cause a fluid to flow out of the outlet at a first flow rate that varies periodically between a first maximum and a first minimum at a first frequency; and
manipulating a second portion of the at least partially compressible pumping element that is disposed between the first portion and the outlet at a second frequency that is a harmonic of the first frequency, to cause the fluid to flow out of the outlet at a second flow rate that varies periodically about zero, wherein a sum of the first and second flow rates has a second minimum larger than the first minimum, wherein:
peristaltically manipulating the first portion comprises actuating a plurality of pumping actuators coupled to a drive shaft,
manipulating the second portion comprises actuating a plurality of compensation actuators coupled to the drive shaft wherein each of the plurality of compensation actuators is actuated to have an independent displacement profile and has a shape configured to displace a same volume of the fluid as each of the plurality of pumping actuators; and
rotating at least two of the plurality of compensation actuators in phase.

2. The method of claim 1, wherein:
there is a phase offset between the manipulating the first portion of the at least partially compressible pumping element and the manipulating the second portion of the at least partially compressible pumping element.

3. The method of claim 2, wherein a phase offset between the first and second flow rates is in a range of 90°-270°.

4. The method of claim 3, wherein the phase offset between the first and second flow rates is 180°.

5. The method of claim 2, wherein the harmonic of the first frequency comprises at least one higher-order frequency that is an integer multiple of the first frequency.

6. The method of claim 5, wherein the harmonic of the first frequency comprises a frequency that is twice the first frequency.

7. The method of claim 2, wherein the harmonic of the first frequency comprises a frequency that is three times the first frequency.

8. The method of claim 1, wherein the sum of the first and second flow rates at the outlet is greater than zero at all times while pumping the fluid.

9. The method of claim 1, wherein:
actuating the plurality of pumping actuators comprises actuating the plurality of pumping actuators by rotating a plurality of pumping cams with the drive shaft; and
actuating the plurality of compensation actuators comprises actuating the plurality of compensation actuators by rotating a plurality of corresponding compensation cams with the drive shaft.

10. The method of claim 9, wherein rotating the plurality of corresponding compensation cams with the drive shaft comprises rotating the plurality of corresponding compensation cams out of phase and at a common frequency with the plurality of pumping actuators.

11. The method of claim 1, wherein actuating the plurality of compensation actuators comprises actuating the plurality of compensation actuators with a first lift that is smaller than a second lift of any of the plurality of pumping actuators.

12. The method of claim 11, wherein actuating the plurality of compensation actuators further comprises actuating two compensation actuators with a lift.

13. The method of claim 11, wherein actuating the plurality of compensation actuators further comprises:
actuating a first compensation actuator with the first lift; and
actuating a second compensation actuator with a second lift that is smaller than the first lift.

14. The method of claim 1, further comprising rotating the drive shaft at a varying rotational speed, wherein a full cycle of the drive shaft comprises one or more variation periods of the varying rotational speed.

15. The method of claim 1, further comprising rotating the drive shaft at a varying rotational speed with a variable speed transmission coupling a cam wheel attached to the drive shaft with a circular drive wheel, the cam wheel having an asymmetric shape.

16. The method of claim 1, wherein manipulating the second portion comprises using a gear linkage coupled to the plurality of compensation actuators.

17. The method of claim 1, wherein manipulating the first portion comprises controlling the drive shaft with a first motor, and manipulating the second portion comprises controlling the plurality of compensation actuators with a second motor.

18. A pumping mechanism comprising:
a peristaltic pumping mechanism having an inlet and an outlet, the pumping mechanism configured to receive a fluid through the inlet and provide an output flow of the fluid through the outlet at an output flow rate that varies periodically over time about a nominal flow rate, wherein the peristaltic pumping mechanism comprises a first portion comprising a plurality of pumping actuators coupled to a drive shaft, and a second portion comprising a plurality of compensation actuators coupled to the drive shaft, the plurality of compensation actuators configured to actuate independently of the plurality of pumping actuators in the first portion, and having a same shape as the plurality of pumping actuators in the first portion, wherein the plurality of compensation actuators have in phase rotation of at least two of the plurality of compensation actuators; and
a variable volume having an inlet fluidically coupled to the outlet of the pumping mechanism and an outlet, wherein the variable volume is configured to vary synchronously with a periodic variation of the output flow.

19. The pumping mechanism of claim 18, wherein:
a variable volume increases during at least a portion of a time when the output flow rate through the outlet of the pumping mechanism is greater than the nominal flow rate; and
the variable volume decreases during at least a portion of the time when the output flow rate through the outlet of the pumping mechanism is less than the nominal flow rate.

20. The pumping mechanism of claim 19, wherein the plurality of compensation actuators are configured to control the variable volume.

21. A method of pumping a fluid through an intravenous (IV) set having an outlet, the method comprising:
- rotating a drive shaft coupled to a drive motor by rotating the drive motor with a variable speed such that the rotation of the drive motor comprises a fundamental frequency and a modulation frequency that is an integer multiple of the fundamental frequency and the fundamental frequency is determined by an inverse of a time period required for the drive shaft to complete one 360° rotation;
- peristaltically manipulating adjacent sections of a first portion of the IV set when the drive shaft is rotated using a plurality of pumping actuators respectively coupled to a plurality of pumping cams, the plurality of pumping cams being disposed in a row along the drive shaft and coupled to the drive shaft, the plurality of pumping cams having common profiles and arranged as offset cams with common rotational offsets between each pair of adjacent pumping cams, the plurality of pumping cams comprising a last pumping cam;
- selectively compressing a section of a second portion of the IV set that is disposed between the first portion and the outlet using a plurality of compensation actuators coupled to a respective plurality of compensation cams, the plurality of compensation cams fixedly coupled to the drive shaft adjacent to the last pumping cam, the plurality of compensation cams rotationally offset relative to the last pumping cam, wherein peristaltically manipulating adjacent sections of a first portion of the IV set comprises actuating a plurality of pumping actuators coupled to a drive shaft, and independently actuating the plurality of compensation actuators coupled to the drive shaft, the plurality of compensation actuators having a same shape as the plurality of pumping actuators; and
- rotating at least two of the plurality of compensation actuators in phase.

22. The method of claim 21, further comprising modulating an angular speed of the drive shaft using a transmission coupled between the drive motor and the drive shaft.

* * * * *